United States Patent [19]

Benham

[11] Patent Number: 4,554,849

[45] Date of Patent: Nov. 26, 1985

[54] METHOD AND APPARATUS FOR PUNCHING HOLES IN POLYMER TUBES

[75] Inventor: Thomas Benham, Lake Jackson, Tex.

[73] Assignee: Mallinckrodt, Inc., St. Louis, Mo.

[21] Appl. No.: 566,901

[22] Filed: Dec. 29, 1983

[51] Int. Cl.[4] .............................................. B26F 1/38
[52] U.S. Cl. ........................................ 83/40; 83/54;
83/98; 83/192; 83/658; 83/684
[58] Field of Search ..................... 83/30, 54, 178, 179,
83/180–184, 188–194, 660, 658, 684, 98, 99, 40

[56] References Cited

U.S. PATENT DOCUMENTS 2,326,536  8/1943  Hartsock et al. ................. 83/193 X
2,492,384 12/1949  Kaslow .
2,972,779  2/1961  Cowley ............................. 83/54 X
3,781,124 12/1973  Bodycomb et al. ............... 83/658 X
3,995,518 12/1976  Spiroff .............................. 83/54
4,122,590 10/1978  Spencer ............................ 83/54 X
4,129,129 12/1978  Amrine ............................ 128/214

Primary Examiner—James M. Meister
Attorney, Agent, or Firm—Bernard, Rothwell & Brown

[57] ABSTRACT

A polymer tube is inserted into a passageway in a guide block and a polymer support rod is inserted into the tube. Pluralities of tubular punches are simultaneously driven from different radial positions through the wall of the tube and into the support rod to form holes in the tube.

14 Claims, 14 Drawing Figures

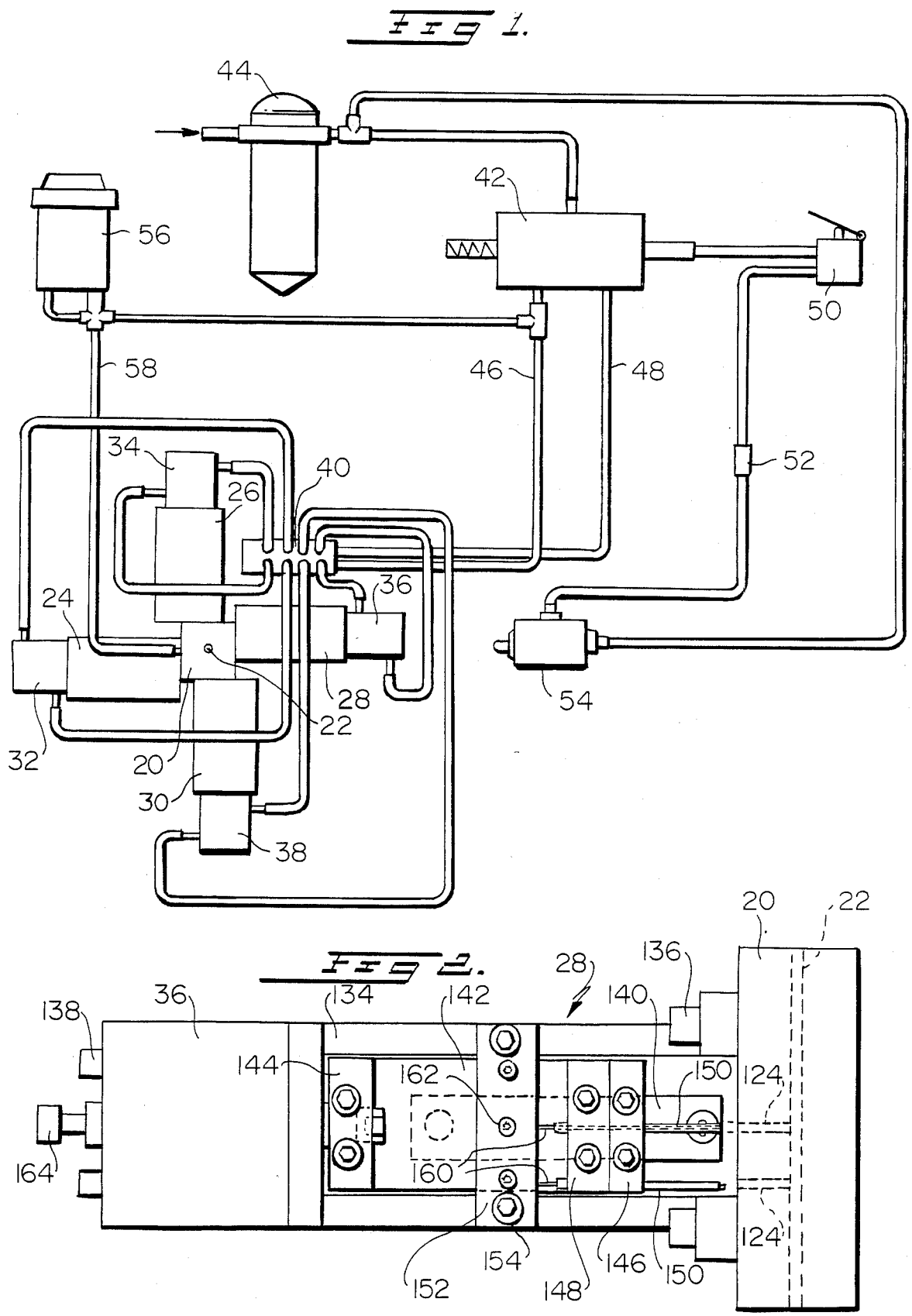

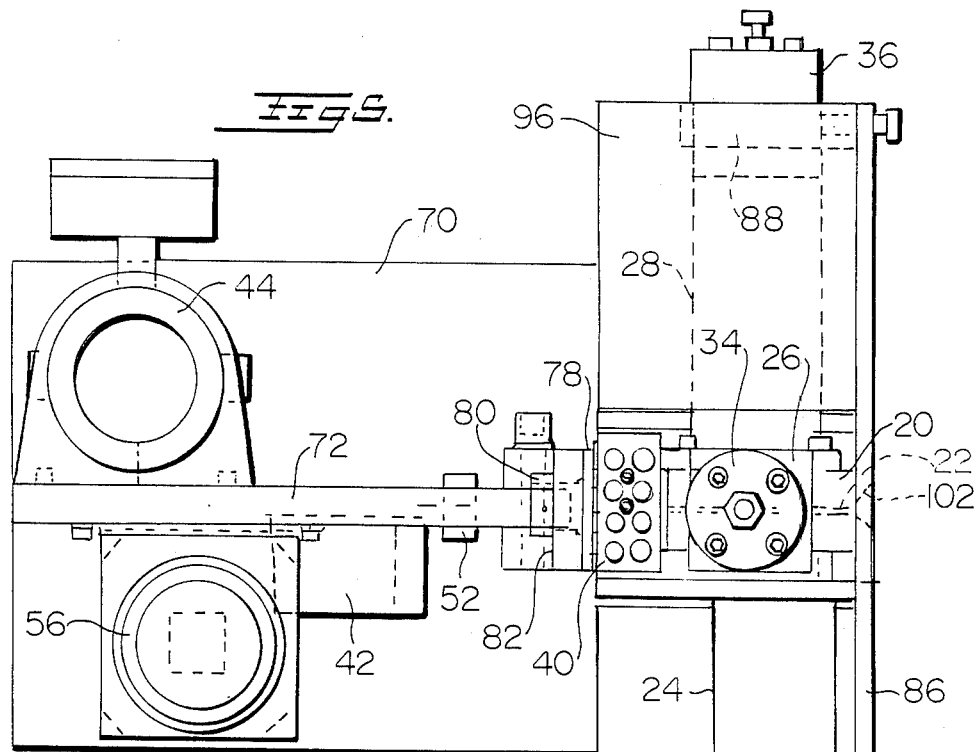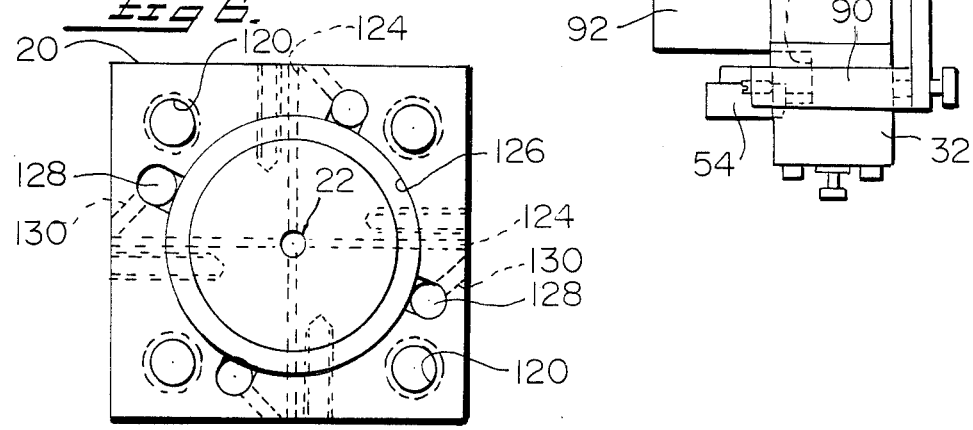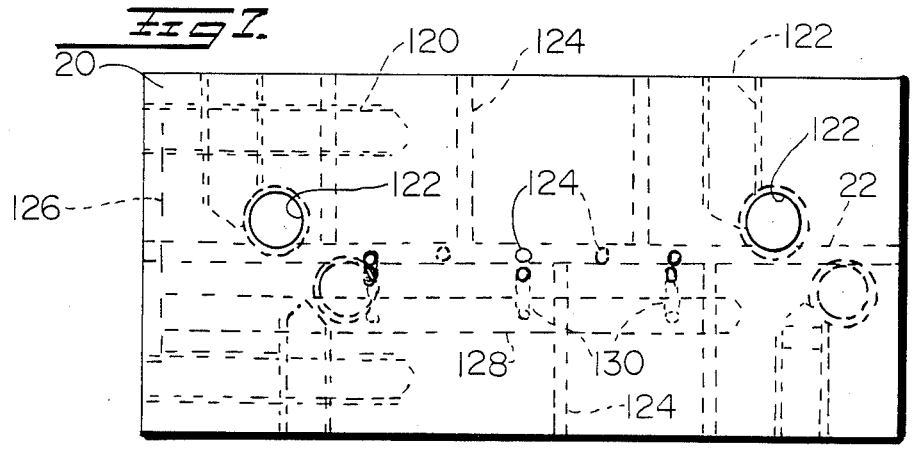

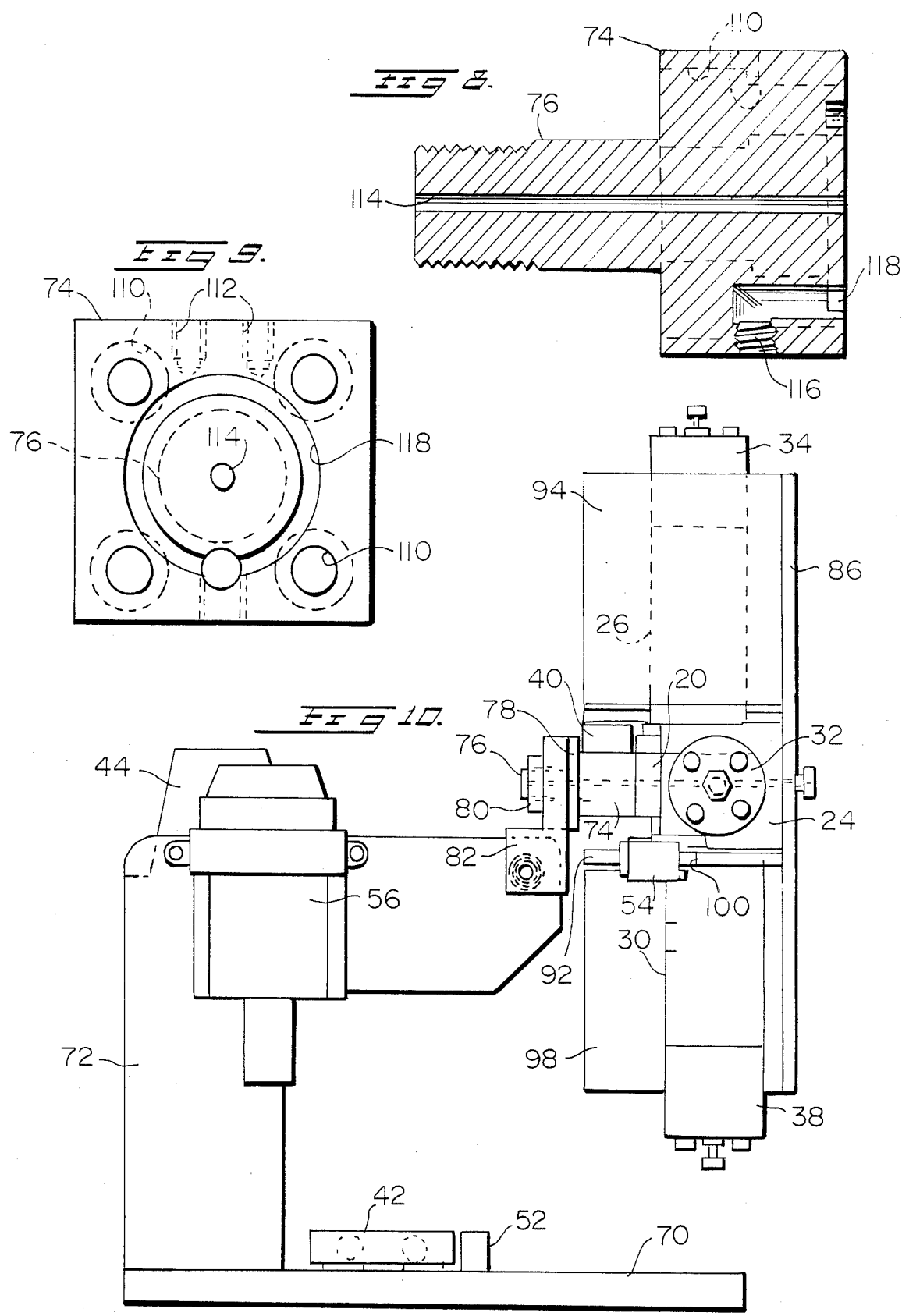

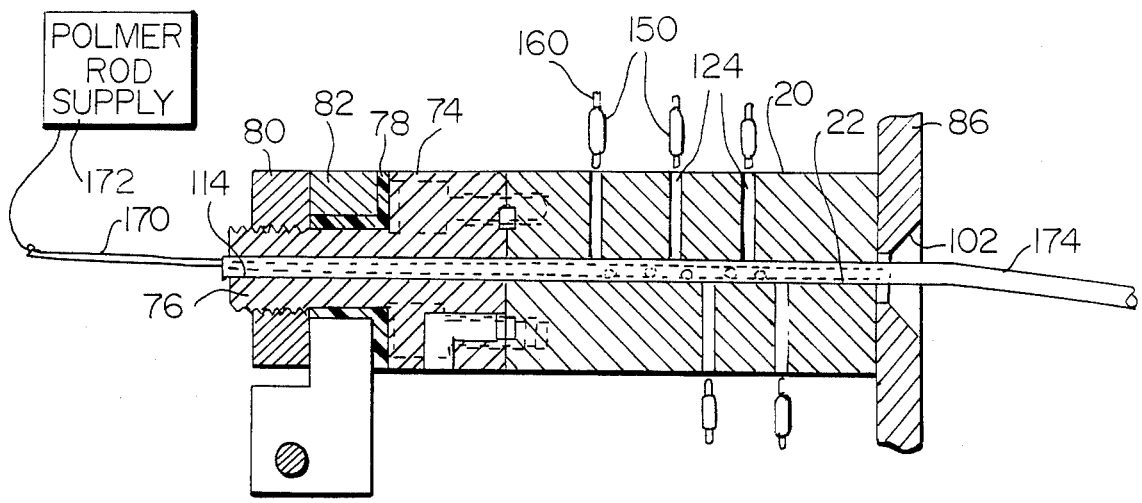
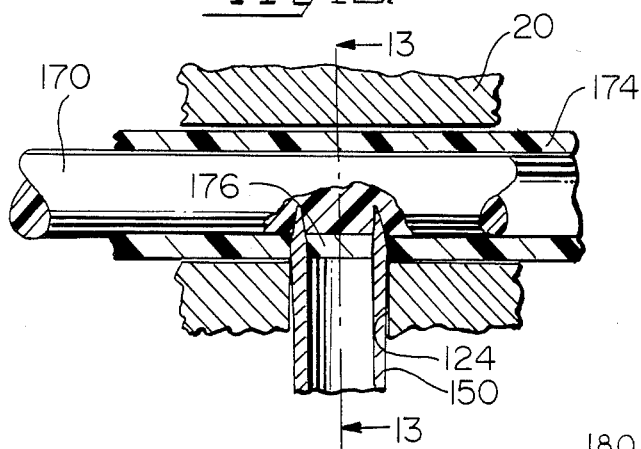
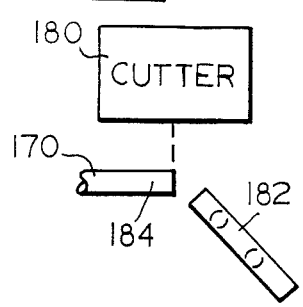
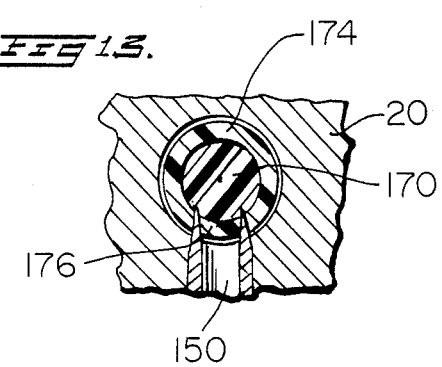

4,554,849

METHOD AND APPARATUS FOR PUNCHING HOLES IN POLYMER TUBES

BACKGROUND OF THE INVENTION

1. Field of the Invention

The present invention relates to methods and apparatus for producing holes in the walls of tubes, such as producing laterally projecting holes in polymeric tubular stock in the manufacture of catheters used in radiographic procedures for diagnosing coronary or other arterial disease.

2. Description of the Prior Art

In the prior art, holes are formed in the walls of tubular catheter stock by using a tubular punch held in a pin vice or hand chuck to enable the tubular punch to be positioned and engaged with the wall of the tubular stock with a twisting and pushing motion to sever a circular portion of the wall and form a hole. Where a plurality of holes are formed within a catheter, each hole is individually formed. The prior art procedures were costly since they required considerable manpower. Also in the prior art, optimum and uniform placement of holes is difficult to obtain, and there is a substantial risk of forming burrs which could traumatize blood vessels, and of forming loose cut material which could be later dislodged and discharged into a blood vessel.

SUMMARY OF THE INVENTION

The invention is summarized in a method and apparatus for punching holes in walls of polymer tubes wherein a section of tube is positioned within a guideway extending through a punch mount, a section of polymer rod is inserted into the interior of the tube section, and one or more tubular punches are driven through the wall of the tube section into the polymer rod to sever a hole piece from the tube wall and to force the severed hole piece into the tubular punch. The tubular punch or punches are then withdrawn leaving a hole or holes in the wall of the tube section.

An object of the invention is to provide a method and apparatus for forming holes in walls of flexible polymer tubes with substantially reduced manpower and cost.

Another object of the invention is to automatically form a plurality of holes in a tubular stock with a desired and uniform spacing.

One advantage of the invention is that employment of a polymer rod as an inside mandrel in a tube being punched enables the formation of smooth, clean-cut holes eliminating burrs and formation of loose-cut material.

Another advantage of the invention is that productivity may be increased up to twenty-five times.

One feature of the invention is that the employment of a disposable section of polymer rod as an internal mandrel during punching enables the tubular punch to cut into the rod ensuring a clean and complete cut of a polymer hole portion to form a hole in the tube wall.

Other objects, advantages and features of the invention will be apparent from the following description of the preferred embodiment taken in conjunction with the accompanying drawings.

BRIEF DESCRIPTION OF THE DRAWINGS

FIG. 1 is a diagram of an overall apparatus for punching a plurality of holes in a section of tubular catheter stock in accordance with the invention.

FIG. 2 is a plan view with the rear being at the bottom and the at the top of a punch assembly in the apparatus of FIG. 1.

FIG. 5 is a plan view of the apparatus of FIG. 3.

FIG. 6 is a rear view of a tube guide and punch mount block in the apparatus of FIGS. 1, 3, 5, and 10.

FIG. 7 is a side elevational view, taken from the left side, of the block of FIG. 6.

FIG. 8 is a section view, taken from the left side, of a block support member in the apparatus of FIGS. 3, 5, and 10.

FIG. 9 is a rear elevational view of the support member of FIG. 8.

FIG. 10 is a side elevation view, taken from the left side, of the apparatus of FIGS. 3 and 5.

FIG. 11 is a section view, taken from the left side, of a tube receiving subassembly broken away from the apparatus of FIGS. 3, 5, and 10.

FIG. 12 is an enlarged section view, taken from the left side, of a portion of the guideblock and the tubular punch of FIG. 11, particularly illustrating the formation of a hole.

FIG. 13 is a cross section view taken at line 13-13 in FIG. 12.

FIG. 14 is a diagrammatic view illustrating severing of a marred rod end section.

DESCRIPTION OF THE PREFERRED EMBODIMENT

Figure 3:
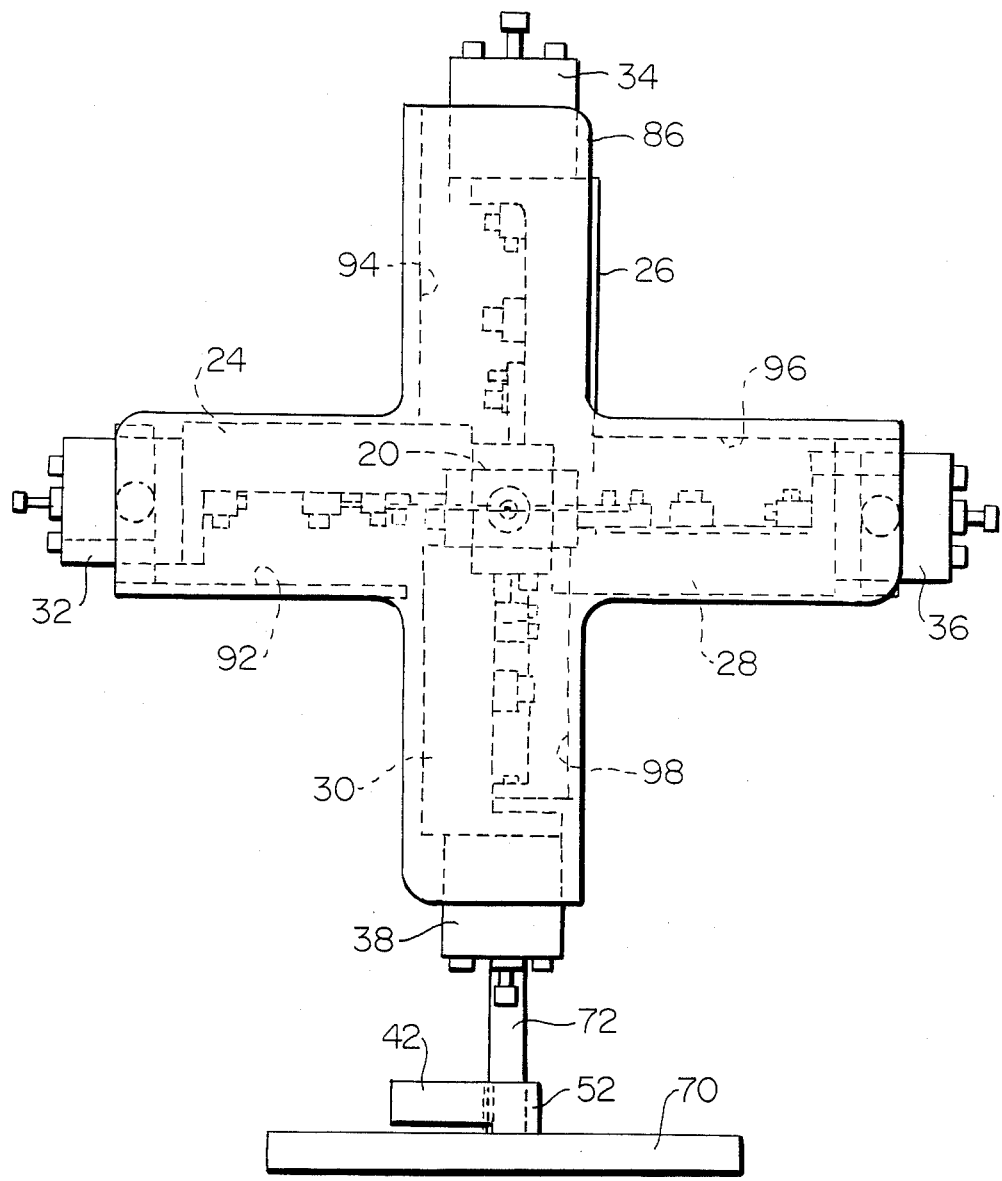
FIG. 3 is a front view, with hoses removed, of the mechanical portions of FIG. 1.

As shown in FIG. 1, one embodiment of an apparatus for punching holes in the walls of catheter tubing stock in accordance with the invention includes a guide and punch mounting block 20 with a central passage or guideway 22 for receiving a section of the catheter tube to be punched, and four punch assemblies 24, 26, 28 and 30 mounted on respective sides of the block 20. Each punch assembly has a corresponding air cylinder 32, 34, 36 and 38 with an advance inlet connected to the advance side of a dual manifold 40 and has a retract inlet connected to the retract side of the manifold 40. An air-actuated, spring-return, four-way valve 42 has its inlet connected to a air pressure regulator 44 receiving air from a suitable supply, and has its normally open output connected by line 46 to the retract side of the manifold 40 and its normally closed output connected by line 48 to the advance side of the manifold 40. The actuating input of the valve 42 is connected to the normally closed outlet of a foot-actuated three-way valve 50 which has its inlet connected to lines through a manifold bracket 52 and a normally closed safety valve 54 to the outlet of the regulator 44; the safety valve 54 being open when guards are properly installed. The normally opened outlet of the valve 42 on line 46 is also connected through a T connector to the inlet of a normally opened timer valve 56 which has its outlet connected through line 58 to a blowoff inlet to the block 20. Operation of the foot valve 50 operates valve 42 which in turn advances the air cylinders 32, 34, 36, and 38 to operate the punch assemblies 24, 26, 28 and 30, and release of the valve 50 results in return of the valve 42 which causes return of the air cylinders 32, 34, 36 and 38 and also applies a momentary air pressure through timer valve 56 and line 58 to the blowoff inlet of block 20.

As shown in FIGS. 3, 5 and 10, the apparatus has a base plate 70 upon which is mounted the valve 42 and the bracket manifold 52 along with a vertical support arm 72 on which are mounted the pressure regulator 44 and the timer valve 56. The tube guide and punch mounting block 20 is mounted on a forward extending portion of the arm 72 by means of a support member 74 which has a shank portion 76 secured by a bushing 78 and a nut 80 to a swivel bracket 82 mounted on the forward end of the arm 72. The manifold 40 is mounted on top of the support member 74.

A safety guard such as a clear plastic guard 86 is removably secured to brackets 88 and 90 secured by set screws on the air cylinders 32 and 36. The guard has a cross-like configuration covering the front portion of the radially-extending punch mechanisms and has rearward wings 92, 94, 96 and 98 covering portions of the punches to prevent an operator's fingers from being injured by the punch mechanism. The safety valve 54 is mounted on the bracket 90 and has its operator engaged by an edge 100 of the wing 92 for opening the valve 50 when the guard is in place whereby the valve 54 prevents operation of the apparatus when the guard is removed. An opening 102 is formed in the guard 86 in alignment with the opening 22 in the block 20 for permitting the catheter tubular stock material to be inserted into the passage 22.

The support member 74, as shown in FIGS. 8 and 9, includes suitable recessed bolt bores 110 for receiving mounting bolts which secure the block 20 to the support member 74 and include threaded bores 112 for receiving mounting bolts which mount the manifold 40 thereon. A central passage or bore 114 is formed through the member 74 in alignment with the passage 22 in the member 20 for receiving the end portion of a catheter tubular stock material. An inlet bore 116 is provided for connecting to the hose 58 of FIG. 1, and communicates with an annular channel 118 on the forward face of the member 74 which mates with the member 22 for supplying blowoff air to the guideblock 20.

The block 20 as shown in FIGS. 6 and 7 has threaded bores 120 extending from the rear face for the mounting bolts from support member 74, and has threaded bores 122 suitably formed in each of the right, left, upper, and lower sides thereof for receiving mounting bolts mounting the respective punch asssemblies 24, 26, 28 and 32 thereto. Openings or bores 124 are formed in each of the right, left, upper, and lower sides of the block 20 and extend into the guidepassage 22 for receiving and directing respective punches. The bores 124 are formed in the desired pattern for holes to be produced in the catheter stock. In the example, three bores are shown from each of the top and left sides, and two bores are shown from each of the right and lower sides with the spacing of the holes being generally uniform. An annular channel 126 is formed in the rear face of the member 20 for mating with the channel 118 of the support member 74. Longitudinal bores 128 are formed in the block and communicate at the rear end of the block with the channel 126. Bores 130 extend obliquely to each of the sides of the block 20 into corresponding bores 128; the bores 130 being directed obliquely from the corresponding sides of the block 20 over corresponding openings 124 for directing blowoff air to remove the cut wall material from the region over the openings 124.

Figure 4:
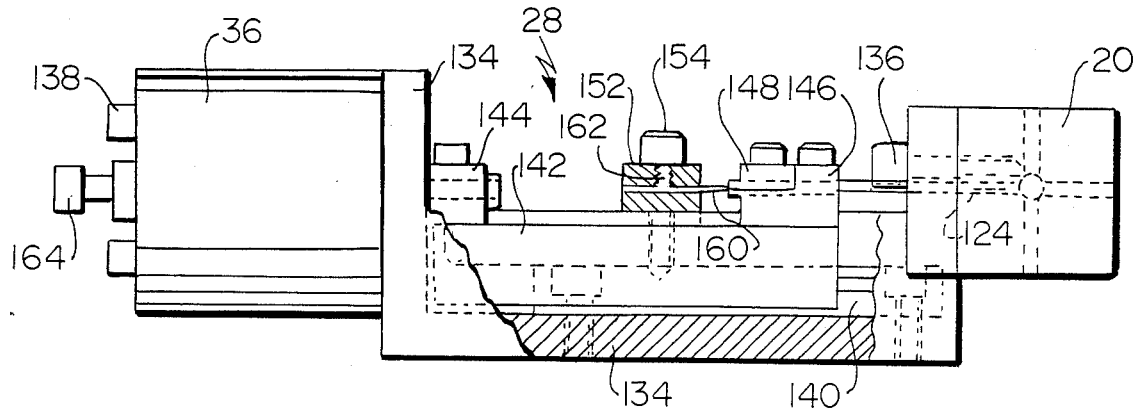
FIG. 4 is a rear elevation view of the punch assembly of FIG. 2.

The punch assemblies 24, 26, 28 and 30 are substantially similar to each other, differing only in the number and possible positioning of punches therein. The punch assembly as shown in FIGS. 2 and 4 includes a housing 134 mounted at one end by bolts 136 on the block 20 and having the air cylinder mounted by bolts 138 on the opposite end of the housing. A ball slide assembly includes a stationary rail portion 140 mounted in the bottom of a channel formed in the housing 134 with a movable member 142 slidably mounted on the rail portion 140. One end of the movable slide member 142 is attached by a connector 144 to the piston rod of the air cylinder 36. A holder 146 is mounted on the other end of the slide member 142 by bolts and has as a clamp 148 secured by bolts therein and clamping a pair of tubular punches 150 to the holder 146. The tubular punches 150 are aligned with bores 124 in the block 20. The tubular punches 150 have their distal cutting edges sharpened, for example by electropolishing. A stationary bar 152 is secured by bolts 154 to the side walls of the channel portion of the housing 134, and have pin stripping members 160 secured within suitable bores therein by set screws 162. The pin stripping members 160 extend into the respective punches 150 so that when the punches 150 are in the retracted position, the stripping pins 160 protude just beyond the cutting edge of the punches 150 to thus strip the cut portion of tube wall from the punches when the punches are retracted. An adjustable stop 164 determines the return position of the air cylinder 36 to thus determine the retracted position of the punches 150.

The present invention utilizes a disposable polymer rod supply which may for example be a continuous rod supply such as a monofilament 170, FIG. 11, from a continuous reel or supply 172. The polymer rod 170 has a diameter selected to readily slip into the interior passage of the catheter tube stock 174. The rod material 170 is selected to have a rigidity which is greater than the rigidity of the material of the tube stock to provide support during punching as well as to permit the cutting edge of the punches 150 to penetrate into the polymer rod. The polymer rod 170 must be sufficiently soft to enable the cutting edges of the punches 150 to penetrate into the rod without dulling the cutting edge. Polyethylene rod material is found suitable for nylon or polyurethane tubular catheter stock. A suitable cutter or knife 180, FIG. 14, is provided for cutting off the section 182 of polymer rod marred by the punches 150, after the polymer rod 170 is pulled from the tube 174.

In operation of the apparatus of FIGS. 1-13 to form holes in catheter stock in accordance with the invention, an operator inserts a leading end section of a catheter tubing stock 174 through the opening 102 in the guide 86 and into the guideway or passage 22 through the block 20. The tubing stock 174 is pushed or threaded through the passages 22 and 114 until the end is flush or slightly protudes from the rear of the support member 74 as shown in FIG. 11. Then the end of the polymer rod 170 is threaded into the leading end of the tube 174 sufficiently to extend past the punches 150. Foot valve 50 is operated causing the valve 42 to apply air to the air cylinders 32, 34, 36 and 38 to simultaneously operate the punch assemblies 24, 26, 28 and 30. Operation of the air cylinders, as shown for the air cylinder in FIGS. 2 and 4, advances the slide 142 and the tubular punches 150. The punches 150 enter the passages 124 of the block 20 engaging the wall of the tube 174, as shown in FIGS. 12 and 13. The punches 150 are set to penetrate through the wall 174 and into the polymer rod 170. The rigidity of the polymer rod 170 prevents collapse of the tube wall and ensures a clean complete cut of a circular segment 176 of the wall of the tube 174. The penetration of the cutting edges of the punch 150 into the rod 170 ensures that the segment 176 is forced into the punch 150. Release of the foot valve 50 results in the valve 42 returning under its spring bias to apply air pressure to the return side of the air cylinders and retract the punches 150. When the punches 150 reach their fully retracted position, the stripping pins 160 push the segments 176 from the tubular punches 150. The air, applied to the return line 46, is also applied through the timer valve 56 to line 58. This applies air through inlet 116 into the annular channel 118 of the member 74 and annular channel 126 of the block 20 which supplies air to bores 128 and the passages 130 directing jets of air tangentially over the openings of the passages 124. These jets of air blow the severed segments 176 away from the entrance of the passages 124 to avoid any interference with subsequent operation. The polymer rod 170 is pulled from the punched tube stock 174, and as shown in FIG. 14, the end section 182 of the rod, which has been marred by the punches 150, is cut off by cutter 186 to present a new unmarred rod end section 184 for insertion in the next catheter tube to be punched. The punched catheter tube 174 after pulling from the apparatus is further formed and processed in a conventional manner to form a catheter.

In employment of the apparatus of FIGS. 1–13, an increase in production of punched tubular stock from about 200 per day per operator to about 5,000 per day per operator has been experienced over the prior method of manually punching each individual hole. Thus, a substantial reduction in the cost of forming catheters has been achieved.

Since many modifications, variations and changes in detail may be made to the above-described embodiment, it is intended that all matter described in the foregoing description and shown in the accompanying drawings be interpreted as illustrative and not in a limiting sense.

What is claimed is:

1. A method of punching a hole in a wall of a section of a polymer tube, comprising
   inserting the polymer tube section into a guideway extending through a punch mount,
   inserting an end section of a continuous supply of monofilament polymer rod into the tube section,
   driving a tubular punch through the wall of the tube section in the guideway and into the polymer rod end section to sever a hole piece from the tube wall and to force the severed hole piece into the tubular punch,
   withdrawing the tubular punch and hole piece to form a hole in the wall of the tube section, and
   severing the end section of the monofilament so as to present an unmarred polymer rod end section for a subsequent punching.

2. A method as claimed in claim 1 wherein the polymer material of the rod has substantially greater rigidity than the polymer material of the tube.

3. A method as claimed in claim 2 wherein the polymer rod is formed from polyethylene, and the polymer tube is formed from nylon or polyurethane.

4. A method of punching a plurality of holes in a wall of a section of a polymer tube, comprising
   inserting the tube section into a central passageway extending through a punch mount block,
   inserting an end section of a continuous supply of monofilament polymer rod into the tube section,
   driving a plurality of tubular punches through bores from different directions in the guideblock to force the tubular punches through the wall of the tubular section and into the polymer rod at different angular positions to sever hole pieces from the tube wall and to force the severed hole pieces into the tubular punches,
   withdrawing the tubular punches and hole pieces to form holes at different angles in the wall of the tube section, and
   severing the end section of the monofilament polymer rod so as to present an unmarred polymer rod section for a subsequent punching.

5. A method as claimed in claim 4 wherein the polymer material of the rod has substantially greater rigidity than the polymer material of the tube.

6. A method as claimed in claim 5 wherein the polymer material of the rod is formed from polyethylene, and the polymer tube is formed from nylon or polyurethane.

7. An apparatus for punching a hole in a wall of a section of a polymer tube, comprising
   a punch mount having a guideway therein for receiving the polymer tube section,
   means for supplying an end section of a continuous supply of monofilament polymer rod for insertion into the polymer tube section,
   a tubular punch,
   means supporting the tubular punch for driving the tubular punch through the wall in the polymer tube section and into the polymer rod to sever a hole portion from the polymer tube section and to force the severed hole portion into the tubular punch and for withdrawing the tubular punch to form a hole in the wall of the polymer tube section, and
   means for severing the end sectron of the monofilament polymer rod so as to present an unmarred polymer rod section for a subsequent punching.

8. An apparatus as claimed in claim 7 including a plurality of tubular punches and tubular punch supporting means mounted in different radial positions in a radial arrangement on the punch mount for severing a plurality of holes at different angular positions in the wall of the polymer tube section.

9. An apparatus as claimed in claim 7 including a plurality of spaced tubular punches supported by the supporting means for forming a plurality of holes spaced along the length of the polymer tube section.

10. An apparatus as claimed in claim 8 including a plurality of spaced tubular punches supported by each supporting means for forming a plurality of holes spaced along the length of the polymer tube section at each angular position.

11. An apparatus as claimed in claim 10 including support means, and a support member mounting the punch mount on the support means.

12. An apparatus for punching a hole in a wall of a section of a polymer tube, comprising
   a punch mount having a guideway therein for receiving the polymer tube section;
   means for supplying a section of polymer rod for insertion into the polymer tube section, a plurality of tubular punches, means supporting a plurality of tubular punches in respective different radial positions in a radial arrangement on the punch mount for driving the tubular punches through the wall in the polymer tube section and into the polymer rod to sever hole portions from the polymer tube section and to force the severed hole poritons into the tubular punches and for withdrawing the tubular punches to form holes in the wall of the polymer tube section, apparatus support means, a support member mounting the punch mount on the apparatus support means, said support member including a blowoff air inlet and a passage means in a face engaging the punch mount, said punch mount including face channel means communicating with the channel means of the support member, and bore means formed therein communicating with the channel means together with laterally projecting bores opening at oblique angles to openings for the punches, a plurality of pin strippers extending into the respective plurality of tubular punches for stripping the severed hole pieces from the hollow tubular sections when the punches are withdrawn, and means for supplying air pressure through the blowoff inlet to drive air through the bores and the oblique passages to blow the cut pieces from the path of the tubular punches.

13. An apparatus as claimed in claim 12 wherein the blowoff means includes timer valve means operated upon return pressure being applied to the punch operating means to apply a short duration of air pulse to the blowoff inlet.

14. An apparatus as claimed in claim 12 including a plurality of spaced tubular punches supported by each supporting means for forming a plurality of holes spaced along the length of the polymer tube section at each angular position.

* * * * *